United States Patent [19]

Chen et al.

[11] Patent Number: 5,037,409

[45] Date of Patent: Aug. 6, 1991

[54] ABSORBENT ARTICLE HAVING A HYDROPHILIC FLOW-MODULATING LAYER

[75] Inventors: Franklin M. C. Chen; Andrew E. Huntoon, both of Appleton; Duane G. Uitenbroek, Little Chute; Anthony J. Wisneski, Kimberly, all of Wis.

[73] Assignee: Kimberly-Clark Corporation, Neenah, Wis.

[21] Appl. No.: 551,335

[22] Filed: Jul. 12, 1990

[51] Int. Cl.⁵ ............................................. A61F 13/16
[52] U.S. Cl. ......................................................... 604/358
[58] Field of Search .................. 604/358, 365–377, 604/378–385.2

[56] References Cited

U.S. PATENT DOCUMENTS

| | | | |
|---|---|---|---|
| 2,761,449 | 9/1956 | Bletzinger | 128/285 |
| 3,016,599 | 1/1962 | Perry | 28/78 |
| 3,308,826 | 3/1967 | Blake | 128/290 |
| 3,369,544 | 2/1968 | Crockford | 128/285 |
| 3,523,536 | 8/1970 | Ruffo | 128/287 |
| 3,592,194 | 7/1971 | Duncan | 128/287 |
| 3,595,235 | 7/1971 | Jespersen | 128/284 |
| 3,612,055 | 10/1971 | Mesek et al. | 128/287 |
| 3,663,348 | 5/1972 | Liloia et al. | 161/116 |
| 3,665,921 | 5/1972 | Stumpf | 128/287 |
| 3,730,184 | 5/1973 | Mesek | 128/287 |
| 3,768,118 | 10/1973 | Ruffo et al. | 19/156.3 |
| 3,768,480 | 10/1973 | Mesek et al. | 128/287 |
| 3,772,417 | 11/1973 | Vogt | 264/230 |
| 3,777,758 | 12/1973 | Mesek et al. | 128/284 |
| 3,806,289 | 4/1974 | Schwarz | 425/72 |
| 3,837,343 | 9/1974 | Mesek | 128/287 |
| 3,871,378 | 3/1975 | Duncan et al. | 128/290 |
| 3,908,659 | 9/1975 | Wehrmeyer | 128/287 |
| 3,927,673 | 12/1975 | Taylor | 128/287 |
| 3,945,386 | 3/1976 | Anczurowski | 128/287 |
| 3,952,124 | 4/1976 | Mesek | 128/287 |
| 3,965,905 | 6/1976 | Schoenholz et al. | 128/285 |
| 3,965,906 | 6/1976 | Karami | 128/287 |
| 3,978,185 | 8/1976 | Buntin et al. | 264/93 |
| 3,987,792 | 10/1976 | Hernandez | 128/284 |
| 4,014,341 | 3/1977 | Karami | 128/287 |
| 4,018,862 | 4/1977 | Saito | 264/137 |
| 4,041,951 | 8/1977 | Sanford | 128/287 |
| 4,044,768 | 8/1977 | Mesek et al. | 128/287 |
| 4,045,833 | 9/1977 | Mesek et al. | 5/335 |
| 4,077,410 | 3/1978 | Butterworth et al. | 128/287 |
| 4,103,058 | 7/1978 | Humlicek | 428/171 |
| 4,118,531 | 10/1978 | Hauser | 428/224 |
| 4,212,302 | 7/1980 | Karami | 128/287 |
| 4,216,772 | 8/1980 | Tsuchiya et al. | 128/284 |
| 4,223,677 | 9/1980 | Anderson | 128/287 |
| 4,232,674 | 11/1980 | Melican | 128/287 |
| 4,238,175 | 12/1980 | Fujii et al. | 425/83.1 |
| 4,259,958 | 4/1981 | Goodbar | 128/287 |
| 4,285,342 | 8/1981 | Mesek | 128/287 |

(List continued on next page.)

FOREIGN PATENT DOCUMENTS 0108637 5/1984 European Pat. Off. .
0165807 12/1985 European Pat. Off. .
0174775 3/1986 European Pat. Off. .
0193309 9/1986 European Pat. Off. .

(List continued on next page.)

*Primary Examiner*—Randall L. Green
*Assistant Examiner*—K. Reichle
*Attorney, Agent, or Firm*—Thomas J. Mielke

[57] ABSTRACT

An absorbent article including an absorbent body capable of absorbing a liquid and a flow-modulating layer in liquid communication with the absorbent body. The flow-modulating layer is formed from hydrophilic melt-blown fibers having an average diameter of from about 20 to about 60 microns. The flow-modulating layer has an average pore size of from about 90 to about 300 microns and a basis weight of from about 50 to about 600 grams per square meter. The average pore size of the absorbent body is less than the average pore size of the flow-modulating layer. The flow-modulating layer is capable of rapidly receiving multiple liquid insults and distributing the liquid in its X-Y plane prior to said liquid being absorbed by the absorbent body.

28 Claims, 4 Drawing Sheets

U.S. PATENT DOCUMENTS

| | | | |
|---|---|---|---|
| 4,304,234 | 8/1981 | Hartmann | 128/287 |
| 4,324,247 | 4/1982 | Aziz | 128/287 |
| 4,338,371 | 7/1982 | Dawn et al. | 428/283 |
| 4,364,992 | 12/1982 | Ito et al. | 428/283 |
| 4,372,312 | 2/1983 | Fendler et al. | 128/290 |
| 4,374,888 | 2/1983 | Bornslaeger | 428/198 |
| 4,381,611 | 5/1983 | Wishman | 34/9 |
| 4,381,782 | 5/1983 | Mazurak et al. | 604/368 |
| 4,392,861 | 7/1983 | Butterworth et al. | 604/366 |
| 4,392,862 | 7/1983 | Marsan et al. | 604/366 |
| 4,397,644 | 8/1983 | Matthews et al. | 604/378 |
| 4,405,325 | 9/1983 | Antifinger et al. | 604/370 |
| 4,413,032 | 11/1983 | Hartmann et al. | 428/288 |
| 4,421,813 | 12/1983 | Athey | 428/195 |
| 4,436,780 | 3/1984 | Hotchkiss et al. | 428/198 |
| 4,461,621 | 7/1984 | Karami et al. | 604/368 |
| 4,468,428 | 8/1984 | Early et al. | 428/221 |
| 4,480,000 | 10/1984 | Watanabe et al. | 428/284 |
| 4,496,358 | 1/1985 | Karami et al. | 604/379 |
| 4,500,315 | 2/1985 | Pieniak et al. | 604/379 |
| 4,501,586 | 2/1985 | Holtman | 604/380 |
| 4,519,798 | 5/1985 | Dinius | 604/358 |
| 4,519,799 | 5/1985 | Sakurai | 604/366 |
| 4,531,945 | 7/1985 | Allison | 604/378 |
| 4,535,020 | 8/1985 | Thomas et al. | 428/131 |
| 4,537,590 | 8/1985 | Pieniak et al. | 604/379 |
| 4,540,414 | 9/1985 | Wishman | 604/378 |
| 4,540,454 | 9/1985 | Pieniak et al. | 156/62.2 |
| 4,550,725 | 11/1985 | Wishman | 128/155 |
| 4,551,143 | 11/1985 | Cook et al. | 604/371 |
| 4,559,051 | 12/1985 | Hanson | 604/385 |
| 4,560,372 | 12/1985 | Pieniak | 604/369 |
| 4,573,988 | 3/1986 | Pieniak et al. | 604/379 |
| 4,578,066 | 3/1986 | O'Connor | 604/366 |
| 4,578,070 | 3/1986 | Holtman | 604/378 |
| 4,578,414 | 3/1986 | Sawyer et al. | 524/310 |
| 4,590,114 | 5/1986 | Holtman | 428/171 |
| 4,608,292 | 8/1986 | Lassen | 428/131 |
| 4,623,340 | 11/1986 | Luceri | 604/385 |
| 4,623,576 | 11/1986 | Lloyd et al. | 428/171 |
| 4,636,209 | 1/1987 | Lassen | 604/378 |
| 4,654,040 | 3/1987 | Luceri | 604/385 |
| 4,655,757 | 4/1987 | McFarland et al. | 604/366 |
| 4,673,402 | 6/1987 | Weisman et al. | 604/368 |
| 4,675,013 | 6/1987 | Ruffo | 604/366 |
| 4,681,577 | 7/1987 | Stern et al. | 604/378 |
| 4,699,619 | 10/1987 | Bernardin | 604/378 |
| 4,699,620 | 10/1987 | Bernardin | 604/378 |
| 4,704,112 | 11/1987 | Suzuki et al. | 604/385 |
| 4,707,398 | 11/1987 | Boggs | 428/224 |
| 4,714,647 | 12/1987 | Shipp, Jr. et al. | 428/212 |
| 4,735,624 | 4/1988 | Mazars | 604/378 |
| 4,738,676 | 4/1988 | Osborn, III | 604/385 |
| 4,755,178 | 7/1988 | Insley et al. | 604/367 |
| 4,755,179 | 7/1988 | Shiba et al. | 604/370 |
| 4,794,034 | 12/1988 | Nishizawa et al. | 428/218 |
| 4,798,603 | 1/1989 | Meyer et al. | 604/378 |
| 4,923,454 | 5/1990 | Seymour et al. | 604/368 |

FOREIGN PATENT DOCUMENTS

| | | |
|---|---|---|
| 0254476 | 1/1988 | European Pat. Off. |
| 0317058 | 5/1989 | European Pat. Off. |
| 3525379 | 1/1987 | Fed. Rep. of Germany |
| 61-2854 | 1/1986 | Japan |
| WO80/01455 | 7/1980 | PCT Int'l Appl. |
| WO86/05661 | 9/1986 | PCT Int'l Appl. |
| 1308935 | 3/1973 | United Kingdom |
| 1389891 | 4/1975 | United Kingdom |
| 1402327 | 8/1975 | United Kingdom |
| 1547524 | 6/1979 | United Kingdom |
| 2023068 | 12/1979 | United Kingdom |
| 2055586 | 3/1981 | United Kingdom |
| 2063683 | 6/1981 | United Kingdom |
| 2087240 | 5/1982 | United Kingdom |
| 2089214 | 6/1982 | United Kingdom |
| 2101038 | 1/1983 | United Kingdom |
| 2131699 | 6/1984 | United Kingdom |
| 2145661 | 4/1985 | United Kingdom |
| 2170108 | 7/1986 | United Kingdom |
| 2214201A1 | 8/1989 | United Kingdom |

ABSORBENT ARTICLE HAVING A HYDROPHILIC FLOW-MODULATING LAYER

BACKGROUND OF THE INVENTION

1. Field of the Invention

The present invention relates to an absorbent article, such as a disposable diaper, feminine care pad, adult incontinent garment, training pant, wound dressing, and the like. Specifically, the present invention relates to an absorbent article which includes a hydrophilic flow-modulating layer adapted to receive a liquid and modulate the flow of said liquid prior to the liquid being absorbed by an absorbent body.

2. Description of the Related Art

Conventional absorbent articles typically include an absorbent body comprised of cellulosic fibers such as wood pulp fluff. The absorbent body may, in addition to the wood pulp fluff, contain particles of a high absorbency material which serves to increase the absorbent capacity of the absorbent body. In addition to the absorbent bodies, conventional absorbent articles typically comprise additional layers of material located between the body of a wearer and said absorbent body. Such layers are typically designed to perform the function of separating the body of the wearer from the absorbent body, thereby reducing the skin wetness of a wearer. In order to reduce the skin wetness of a wearer, such layers are typically formed from hydrophobic fibers.

European Patent Application EP 0 165 807A published Dec. 27, 1985, describes a sanitary napkin which includes an apertured top sheet and a resilient layer underlying the top sheet. The absorbent structure can also include a wicking layer between the apertured top sheet and the resilient layer, an absorbent core underlying the resilient layer, and a moisture barrier located against the outermost side of the absorbent core. The resilient layer is described as isolating the apertured top sheet from bodily discharges which have passed through the top sheet and as serving as a reservoir for body discharges.

U.S. Pat. No. 4,798,603 issued Jan. 17, 1989, to Meyer, et al. is directed to an absorbent article having a hydrophobic transport layer. The described absorbent articles comprise an absorbent body, a top sheet layer, and a hydrophobic transport layer. The described hydrophobic transport layer is said to reduce flow back of liquids out of the absorbent body and, as a result, provides less wetness against the skin and greater comfort to a wearer.

When a hydrophobic material is placed between the body of a wearer and an absorbent body, the degree of wetness against the skin of a wearer can, as described above, be reduced. However, the presence of the hydrophobic material may impede the flow of a liquid discharged by the wearer into the absorbent body. That is, while the hydrophobic material may prevent fluid from flowing out of the absorbent body onto the skin of a wearer, it may similarly impede the flow of liquid from a wearer to the absorbent body.

In addition to absorbent articles having hydrophobic materials located between a wearer and an absorbent body, various structures are described which comprise hydrophilic wicking layers in conjunction with an absorbent body. For example, see U.S. Pat. Nos. 4,338,371 issued July 6, 1982, to Dawn, et al.; 4,259,958 issued Apr. 7, 1981, to Goodbar; U.K. Patent Application GB 2 170 108A published July 30, 1986; U.S. Pat. Nos. 4,324,247 issued Apr. 13, 1986, to Aziz; 4,041,951 issued Aug. 16, 1977, to Sanford; 3,945,386 issued Mar. 23, 1976, to Anczurowski, et al.; and 4,413,032 issued Nov. 1, 1983, to Hartmann, et al.

The wicking structures described in the referenced patents are typically formed from a hydrophilic material having a relatively high density and, accordingly, a relatively small pore size. In fact, many of the described wicking structures are formed from wood pulp fluff which has been compressed into relatively high density layers.

While compressed layers of wood pulp fluff are, as described, capable of transporting a fluid, such layers of compressed wood pulp fluff are not generally able to rapidly receive an insult of liquid. Accordingly, such wicking layers are generally located in a manner such that a liquid discharged on the absorbent article can be absorbed by an absorbent body and then wicked throughout said absorbent body. If such wicking layers comprising compressed wood pulp fluff are located between the body of a wearer and an absorbent body, liquids discharged on the absorbent article find it difficult to pass through the wicking layer into the absorbent body at speeds sufficient to prevent leakage from the absorbent articles.

Thus, conventional absorbent articles have not been completely satisfactory. Specifically, the absorbent articles have not been sufficiently able to both rapidly receive and distribute a discharged liquid, thereby modulating the flow of said liquid prior to absorption of the liquid by an absorbent body.

SUMMARY OF THE INVENTION

It is desirable to provide an absorbent article comprising an absorbent structure, which absorbent article is capable of both rapidly receiving multiple discharges of a liquid and of distributing the liquid prior to absorption of the liquid by the absorbent body. It is further desired to provide an absorbent article comprising an absorbent body having a relatively fragile capillary structure, which absorbent article is capable of receiving a liquid discharged thereon without deleteriously affecting a capillary structure of said absorbent body.

These and other related goals are achieved in an absorbent article comprising an absorbent body capable of absorbing a liquid, and a fibrous flow-modulating layer superposed in facing relation to the absorbent body. The flow-modulating layer is in liquid communication with the absorbent body and consists essentially of hydrophilic meltblown fibers having an average diameter of from about 20 to about 60 microns, said flow-modulating layer having an average pore size of from about 90 to about 300 microns, and a basis weight of from about 50 to about 600 grams per square meter. The absorbent body has an average pore size which is less than the average pore size of said flow-modulating layer.

In one preferred embodiment, the absorbent article further comprises a liquid-permeable body-side liner superposed in facing relation to said flow-modulating layer such that the flow-modulating layer is located between said body-side liner and said absorbent body.

BRIEF DESCRIPTION OF THE DRAWINGS

The invention will be more fully understood and further advantages will become apparent when reference is made to the following detailed description of the invention and the following drawings in which.

DETAILED DESCRIPTION OF THE PREFERRED EMBODIMENT

Figure 1:
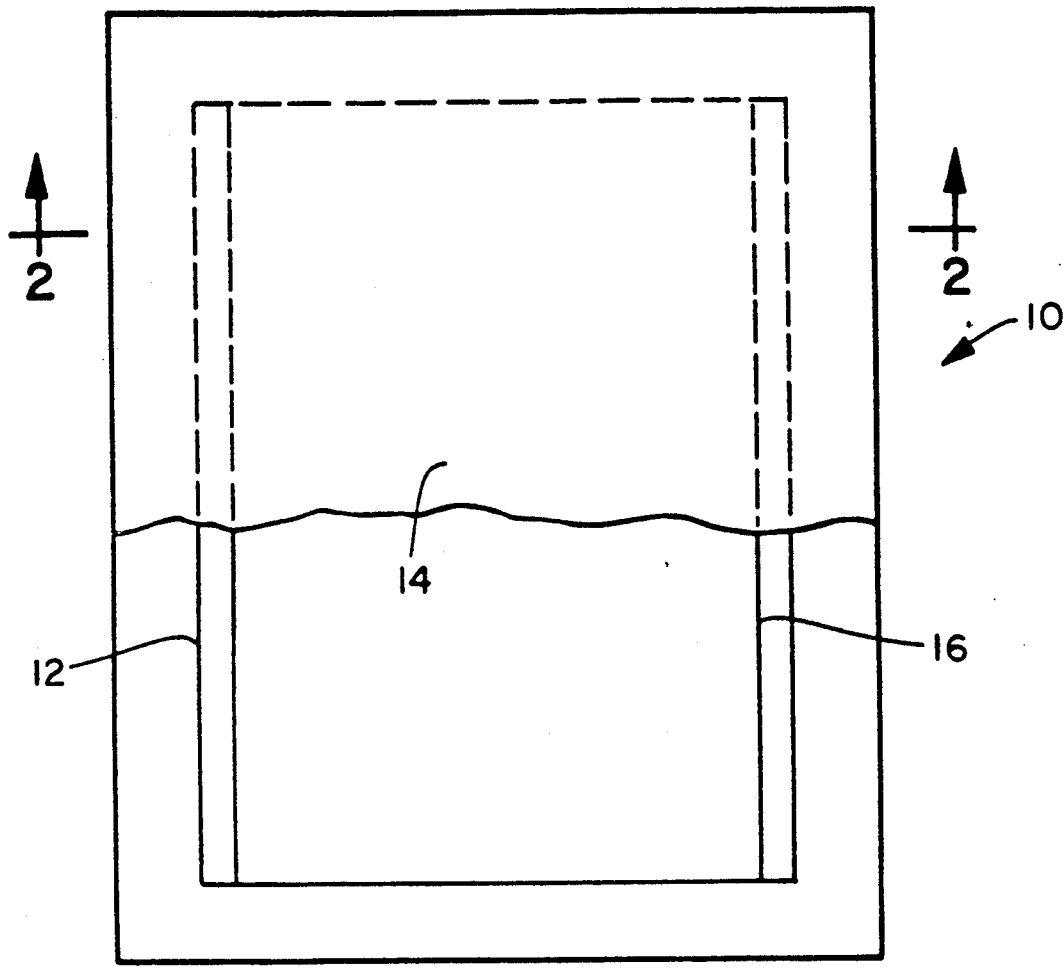
FIG. 1 illustrates a top plan view of an absorbent article according to the present invention.

The following detailed description will be made in the context of a disposable diaper article. It is readily apparent, however, that the absorbent structure of the present invention would also be suitable for other absorbent articles, such as feminine care pads, sanitary napkins, training pants, tampons, adult incontinent garments, wound dressings, and the like. With reference to FIG. 1, an absorbent article 10, includes an absorbent body 12, a liquid-permeable body-side liner 14, and a fibrous flow-modulating layer 16 superposed in facing relation to said absorbent body and located between said body-side liner 14 and said absorbent body 12. The absorbent body 12 is composed of substantially hydrophilic material capable of absorbing a liquid such as urine and other body discharges. The absorbent body has an average pore size therein. The body side liner 14 is superposed in facing relation with a first major surface of the absorbent body. The fibrous flow-modulating layer 16 is located between the absorbent body 12 and the body side liner 14. The flow-modulating layer consists essentially of meltblown hydrophilic fibers and is adapted to receive and distribute a discharged liquid prior to the liquid reaching the absorbent structure. The flow-modulating layer has an average pore size therein which is greater than the pore size of the immediately adjacent portion of the absorbent body 12.

The fibrous flow-modulating layer consists essentially of hydrophilic meltblown fibers having an average diameter of from about 20 to about 60 microns. The flow-modulating layer has an average pore size of from about 90 to about 300 microns and a basis weight of from about 50 to about 600 grams per square meter.

Figure 2:
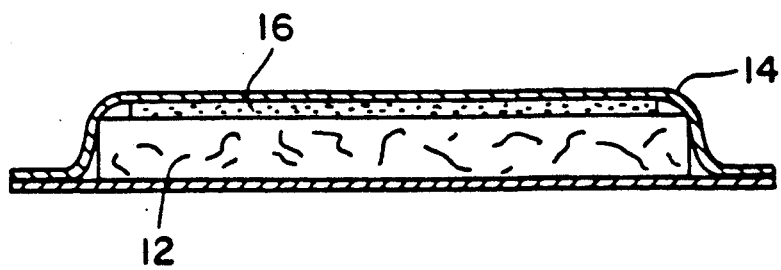
FIG. 2 illustrates a cross-sectional view taken along Line 2—2 of FIG. 1.

FIG. 2 is a cross-sectional view taken along line 2—2 of FIG. 1.

Figure 3:
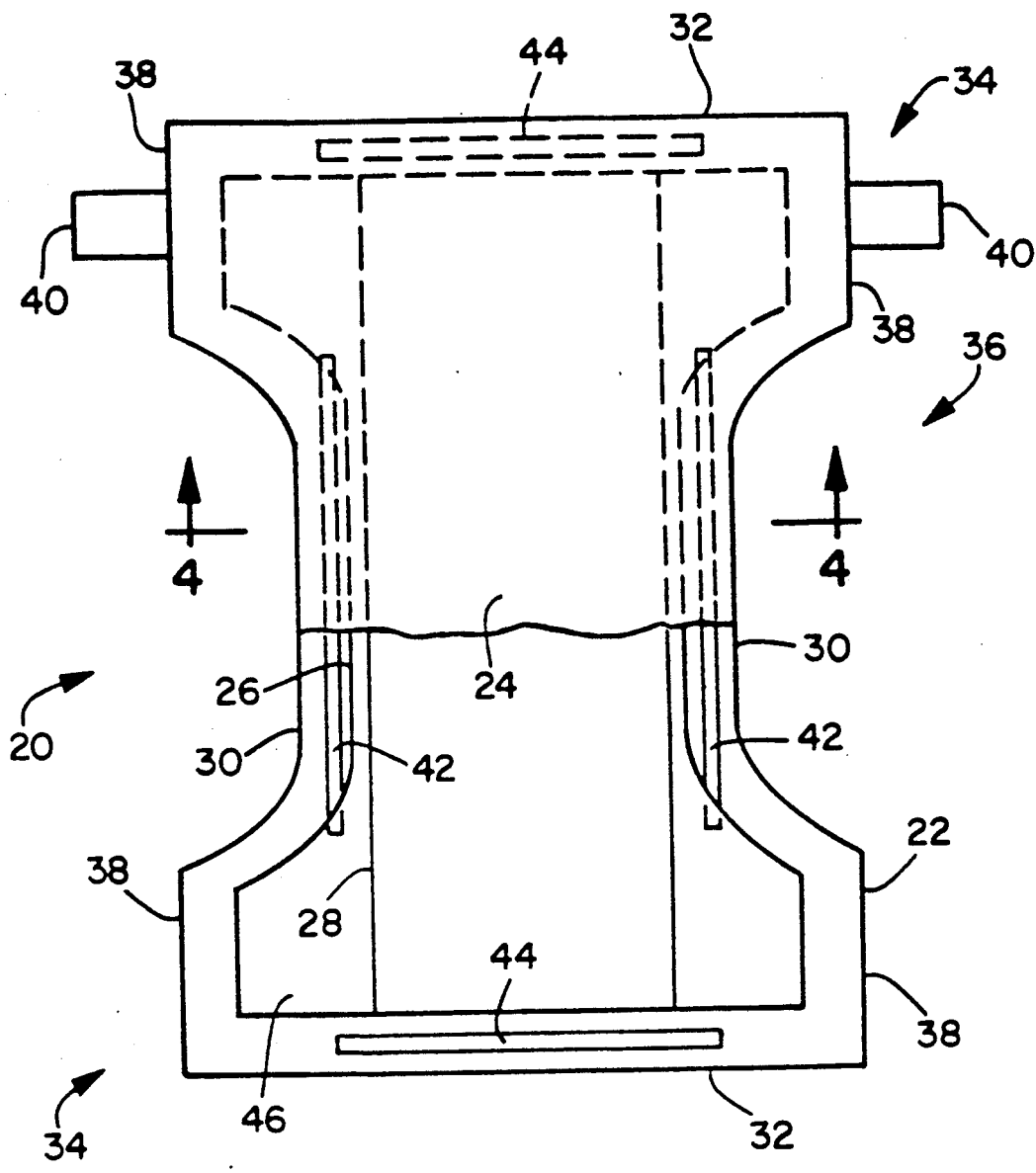
FIG. 3 illustrates an absorbent diaper article of the present invention.
Figure 4:
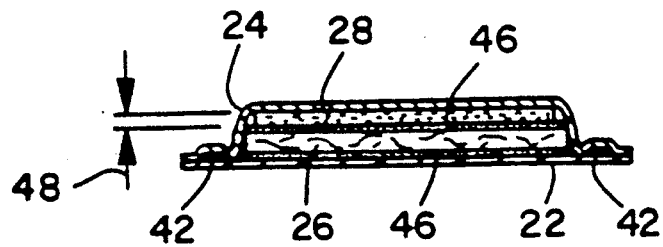
FIG. 4 represents a cross-sectional view taken along Line 4—4 of FIG. 3.

With reference to FIG. 3, an absorbent article such as a disposable diaper 20, includes a back sheet layer 22, and a substantially liquid-permeable body-side liner 24 superposed in facing relation with the back sheet layer 22. An absorbent body 26 composed of a substantially hydrophilic material capable of absorbing a liquid is located between the back sheet layer 22 and the top sheet layer 24; and a fibrous flow-modulating layer 28 consisting essentially of meltblown hydrophilic fibers is located between the body side liner 24 and the absorbent body 26.

The fibrous flow-modulating layer 28 is in liquid communication with the absorbent body 26. The flow-modulating layer will be considered to be in liquid communication with the absorbent body when a liquid applied to said fibrous flow-modulating layer can transfer into the absorbent body. The fibrous flow-modulating layer consists essentially of meltblown hydrophilic fibers having an average diameter of from about 20 to about 60 microns. The fibers define an average pore size of from about 90 to about 300 microns, and the layer has a basis weight of from about 50 to about 600 grams per square meter. The average pore size of the absorbent body is less than the average pore size of the flow-modulating layer such that a liquid applied to the flow-modulating layer will, due to capillary pressure differentials, transfer into the absorbent body.

In the embodiment illustrated in FIG. 3, back sheet 22 and body-side liner 24 are essentially coterminous and extend out past the edges of absorbent body 26 to form marginal edges 30 and 32. The diaper components each have waistband portions 34 interconnected by an intermediate portion 36; and in the illustrated embodiment, the intermediate portion 36 is narrower than the waistband portion. The diaper 20 thus has a generally hourglass or I-shaped plan form with the waistband portion 34 defining ear sections 38 extending oppositely along the lateral cross-wise direction. Two ear sections at one waistband portion of the diaper include securement means for fastening the diaper on the wearer. In the illustrated embodiment, the securement means are operably connected to the back waistband portion of the diaper and comprise adhesive tape tabs 40. It is readily apparent, however, that various other securement means such as hooks, snaps, cohesive strips and the like could also be employed. The diaper illustrated in FIG. 3 further includes elastic members 42, which are attached to each of the diaper's side margins 30 and configured to gather and shirr the leg band portions of diaper 20 to form seals or gaskets about the legs of a wearer.

In addition, the illustrated diaper 20 can include waist elastic members 44 secured to one or more end margins 32 to gather and shirr the waistband portions of the diaper.

The various components of diaper 20 are assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as by spraying droplets or filaments of adhesive. In the embodiment illustrated in FIG. 3, the components are assembled employing a plurality of generally parallel lines of hot melt pressure-sensitive adhesive oriented along the length dimension of the diaper.

In a particular embodiment of the invention, back sheet 22 is composed of a liquid-impermeable material, such as a polymer film. For example, back sheet 22 can be composed of a polyolefin film, such as polyethylene or polypropylene In another embodiment of the invention, back sheet 22 can be composed of a liquid impermeable, but vapor permeable material, such as a breathable, microporous polyethylene film. In yet another embodiment of the invention, the back sheet can be composed of a vapor permeable, nonwoven fibrous material which has been suitably treated to impart a desired degree of liquid impermeability. For example, the back sheet may comprise a nonwoven spunbonded layer which has been completely or partially coated with a polymer film to provide liquid impermeability in particular areas.

Body-side liner 24 is typically composed of a liquid-permeable, substantially hydrophobic fibrous material, such as a spunbonded web composed of synthetic polymer filaments. Alternatively, body-side liner 24 may comprise a meltblown web, a knit web, an apertured film, or a bonded-carded-web composed of synthetic polymer filaments. Suitable synthetic polymers include, for example, polyethylene, polypropylene, and polyesters. In a particular aspect of the invention, the polymer filaments have a denier within the range of about 1.5–7, and preferably have a denier within the range of about 1.5–3. The filaments are arranged to form a layer having a basis weight within the range of about 0.6–1.0 ounce per square yard, and preferably a basis weight of about 0.8 ounce per square yard. In addition, the body-side liner has a bulk thickness within the range of from about 0.008–0.017 inch and preferably a bulk thickness within the range of about 0.010–0.012 inch for improved effectiveness. The bulk thickness is measured under a restraining pressure of 0.014 pounds per square inch. The body-side liner has a pore size that readily allows the passage of liquids, such as urine and other body exudates. A particular aspect of the invention includes a body-side liner having an effective average pore size, in terms of equivalent circular diameter (ECD), which is within the range of from about 40–110 micrometers, and preferably within the range of from about 70–110 micrometers to provide improved effectiveness. Determination of the equivalent circular diameter of a given material will be described in greater detail below in connection with the examples which follow.

Optionally, the body-side liner can be treated with surfactants to adjust its degree of hydrophobicity and wettability, and can also be selectively embossed or apertured with discrete slits or holes extending therethrough. When configured with apertures, the apertures may substantially define the effective pore size of the body-side liner. In a particular aspect of the invention, the apertures have an equivalent circular diameter within the range of from about 160–350 micrometers and preferably have an equivalent circular diameter of about 250 micrometers to provide improved performance.

Absorbent bodies 12 and 26 typically comprise a pad composed of airlaid cellulosic fibers commonly referred to as wood pulp fluff. Conventional pads can have a density within the range of about 0.05 to about 0.3 grams per cubic centimeter as measured under a load of about 0.2 pounds per square inch and are sufficiently flexible to readily conform to the body of the wearer. The absorbent body may also comprise a coform material formed from a mixture of cellulosic fibers and synthetic polymeric fibers or may be formed completely from synthetic polymeric fibers. For example, the coform material may comprise an airlaid blend of cellulosic fibers and a meltblown polyolefin fiber, such as polyethylene and polypropylene fibers. The synthetic polymeric fibers may be formed from a nylon copolymer such as a copolymer formed from nylon 6 and polyethylene oxide diamine. In one aspect of the invention, the absorbent body has a basis weight within the range of from about 400 to about 1200 grams per square meter and preferably has a basis weight of about 900 grams per square meter. In addition, the absorbent body has a bulk thickness within the range of from about 0.05 inch to about 0.9 inch as measured under a restraining pressure of about 0.2 pounds per square inch.

The absorbent bodies according to the present invention may also include an effective amount of an inorganic or organic high-absorbency material to enhance the absorptive capacity of the absorbent body. For example, the absorbent body can include from about 5 to about 99 weight percent of a high-absorbency material.

Suitable inorganic high-absorbency materials include, for example, absorbent clays and silica gels. Organic high-absorbency materials can include natural materials, such as agar, pectin, guar gum, and peat moss; as well as synthetic materials such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Cross linking may, for example, be by irradiation or by covalent, ionic, van der Waals, or hydrogen bonding. Suitable materials are available from various commercial vendors, such as Dow Chemical U.S.A, Hoechst Celanese, Allied Colloids Limited, and Stockhausen, Inc. Typically, the high absorbency material is capable of absorbing at least about fifteen times its weight in an aqueous solution containing 0.9 weight percent of sodium chloride and preferably is capable of absorbing at least about twenty times its weight in an aqueous solution containing 0.9 weight percent of sodium chloride.

The high-absorbency material can be distributed or otherwise incorporated into the absorbent bodies according to the present invention by employing various techniques. For example, the high-absorbency materials can be substantially uniformly distributed in the absorbent body. The material can also be non-uniformly distributed in the absorbent body, for example, a generally continuous gradient with either an increasing or decreasing concentration of high-absorbency material, as determined by observing the concentration moving from the body side of the absorbent body to the outer side of the absorbent body. Alternatively, the high-absorbency material can comprise one or more discrete layers or strips selectively segregated from the material of the absorbent body.

When the absorbent body is formed from airlaid cellulosic fibers, the absorbent body can optionally include a substantially hydrophilic tissue wrap 46 to help maintain the integrity of the airlaid fibrous structure. The tissue wrap sheet typically comprises an absorbent cellulosic material, such as creped wadding or a high wet-strength tissue. In one aspect of the invention the tissue wrap generally provides a continuation of the pore size gradient established between the fibrous flow-modulating layer and the absorbent body. More particularly, the tissue wrap sheet 46 is configured to have an average pore size, as determined by equivalent circular diameter, which is smaller than the average pore size of the flow-modulating layer. In certain preferred embodiments of the present invention, the tissue wrap sheet has an average pore size, in terms of equivalent circular diameter (ECD), which is within the range of from about 10 to about 40 micrometers.

With reference to the embodiment of the invention illustrated in FIGS. 1-4, a fibrous flow-modulating layer is provided in liquid communication with the absorbent body. The flow-modulating layer is located between the absorbent body and the body-side liner and consists essentially of hydrophilic meltblown fibers. Those skilled in the art will recognize what is encompassed by reference to the term meltblown fibers. Methods of forming meltblown fibers are known to those skilled in the art. Generally, such fibers are formed from a thermoplastic synthetic polymeric material which is extruded in the form of fibers and is subjected to attenuation by impinging a stream of air on the extruded fibers. Such a meltblowing process is described in greater detail in U.S. Pat. No. 3,978,185 issued Aug. 31, 1976, to Bunfin et al. which is hereby incorporated by reference.

As used herein, a meltblown fiber will be considered to be hydrophilic when it has a contact angle of water in air of less than 90 degrees, preferably of less than about 50 degrees and most preferably of less than about 10 degrees. The method of determining the contact angle of a meltblown fiber is set forth below in connection with the examples. Suitable hydrophilic fibers may be formed from intrinsically wettable fibers such as nylon copolymers comprising a nylon component and a hydrophilizing component, or may be formed from intrinsically hydrophobic fibers (such as polyolefins) having a surface treatment thereon which renders the fiber hydrophilic. When surface treated fibers are employed to form the flow-modulating layers of the present invention, the surface treatment is desirably nonfugitive. That is, the surface treatment desirably does not wash off the surface of the polymer with the first fluid insult. For the purposes of this application, a surface treatment on a generally hydrophobic polymer will be considered to be nonfugitive when a majority of the fibers demonstrate a water in air contact angle of less than 90 degrees for three consecutive contact angle measurements, with drying between each measurement. That is, the same fiber is subjected to three separate contact angle determinations and if all three of the contact angle determinations indicate a contact angle of water in air of less than 90 degrees, the surface treatment on the fiber will be considered to be nonfugitive. If the surface treatment is fugitive, the surface treatment will tend to wash off of the polymer during the first contact angle measurement thus exposing the hydrophobic surface of the underlying polymer and will demonstrate subsequent contact angle measurements greater than 90 degrees.

The meltblown hydrophilic fibers of the flow-modulating layer have an average diameter of from about 20 to about 60 microns, preferably of from about 25 to about 60 microns, most preferably of from about 40 to about 60 microns. Those skilled in the art will recognize that the required fiber diameters render the fibers relatively large compared to many fibers currently employed in disposable absorbent products. Applicants have discovered that, by using fibers having a relatively large average diameter, the flow-modulating layer is able to retain its pore structure and demonstrates a high degree of resiliency. The average diameter of the fibers of a flow-modulating layer is generally determined by taking a scanning electron micrograph of the fibers, and subjecting said fibers to image analysis. The exact method of determining the average fiber diameters is set forth in greater detail below.

The flow-modulating layers of the present invention define an average pore size of from about 90 to about 300 microns, preferably of from about 100 to about 250 microns. Again, those skilled in the art will recognize that the above-stated average pore sizes are relatively large compared to the pore sizes of many known components of absorbent disposable products. It is generally desired that the flow-modulating layers of the present invention have the described average pore size in order to allow the flow-modulating layers to rapidly receive an insult of a liquid, such as urine.

Finally, the flow-modulating layer of the present invention has a basis weight of from about 50 to about 600 grams per square meter, preferably of from about 100 to about 400 grams per square meter.

Applicants have discovered that flow modulating layers having the characteristics described above are capable of rapidly receiving an insult of a discharged body fluid such as urine or menses, releasing the fluid into the absorbent body and rapidly receiving a subsequent fluid insult. Moreover, the combination of employing a hydrophilic fiber and the other physical characteristics of the flow-modulating layer create a layer which is capable of distributing a liquid discharged thereon in the X-Y plane of the flow-modulating layer. The fluid residual value determined as described below is a measure of the ability of a flow-modulating layer to release a liquid. It is desirable that flow-modulating layers of the present invention have a fluid residual value of less than about 10, preferably less than about 8.

Figure 5:
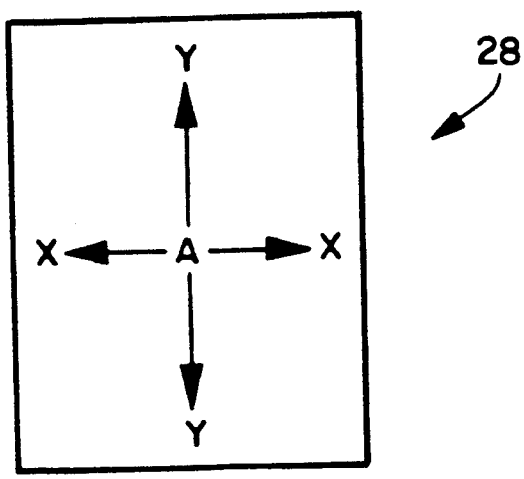
FIG. 5 is a top plan view of a flow-modulating layer according to the present invention.

With reference to FIG. 5, it is seen that a liquid discharged on the flow-modulating layer 28 at point A is distributed in the X-Y plane of the flow-modulating layer 28. Thus, rather than allowing the liquid simply to pass essentially straight through, the flow-modulating layer absorbs much of the force associated with the discharged liquid, dissipates it by spreading the liquid in the X-Y plane of the flow-modulating layer and then allows the liquid to pass into the absorbent body located beneath the flow-modulating layer. This transfer in the X-Y plane aids in preventing the discharged liquid from pooling in the area of the point of application. Since such pooling is believed to lead to leakage, reducing the tendency of the liquid to pool reduces the chance of leakage from an absorbent article.

Further, Applicants have discovered that the capillary structure of the absorbent body can be protected from damage by liquids discharged thereon under a degree of pressure. Specifically, when the absorbent body is formed from a material such as wood pulp fluff, the capillary structure of the absorbent body is subject to collapse when wet.

Collapse of the capillary structure often creates small pores which are slow to absorb subsequent discharges of liquid. If the liquid is applied to the absorbent body under a relatively high pressure, the wet collapse associated with said application is aggravated. If, however, the liquid is applied to the absorbent body under a very low degree of pressure, the wet collapse is kept to a minimum. Thus, while the liquid applied to the flow-modulating layer may be applied to said layer under a degree of pressure, by the time the liquid passes through the flow-modulating layer, the initial pressure of the liquid has been dissipated by transfer of the liquid in the X-Y plane of the flow-modulating layer such that the liquid reaches the absorbent body under a relatively lower degree of pressure. Thus, the capillary structure of the absorbent body is protected.

The liquid applied to the flow-modulating layer must be able to pass into the absorbent body. Accordingly, the absorbent body must be in fluid communication with the flow-modulating layer. Additionally, since transfer of the liquid from the flow-modulating layer into the absorbent body is believed to occur primarily as a result of capillary tension differentials between the flow-modulating layer and the absorbent body, it is desired that the average pore size of the absorbent body adjacent the flow-modulating layer be generally smaller than the average pore size of the flow-modulating layer. In this manner, liquid present in the flow-modulating layer will be drawn into the absorbent body.

Exemplary of materials suitable for use in forming the fibrous flow-modulating layer according to the present invention are inherently wettable polymers and generally nonwettable polymers which have been treated with a surface treatment to render said polymers generally wettable. In one preferred embodiment of the present invention, the fibrous flow-modulating layer is formed from a thermoplastic, hydrophilic nylon copolymer. Suitable thermoplastic hydrophilic nylon polymers comprise a conventional nylon moiety and a hydrophilizing polymer moiety. Nylon polymers are polyamides which can be obtained, for example, by the condensation polymerization of a polyacid and a polyamine. Exemplary of polyamides suitable for use as the nylon moiety of the described hydrophilic nylon copolymers are poly(hexamethylene adipamide) [nylon-6,6]; poly(hexamethylene sebacamide) .[nylon-6,10]; poly(pentamethylene carbonamide) [nylon-6]; poly(decamethylene carbonamide) [nylon-11]; poly(methxylene adipamide) [MXD-6]; bis(para-aminocyclohexyl) methane azelamide [PACM-9]; bis(para-aminocyclohexyl) methane sebacamide [PACM-10]; and bis(para-aminocyclohexyl) methane dodecanoamide [PACM-12]. Methods of preparing polyamides are known to those in the art.

In addition to the nylon (polyamide) moiety, the hydrophilic nylon copolymers comprise a hydrophilizing polymeric moiety. Any polymeric moiety capable of being polymerized with the nylon moiety and capable of hydrophilizing the resultant copolymeric material to render it hydrophilic according to the definition of the present invention is suitable for use in the present invention. One preferred hydrophilizing polymeric moiety suitable for use in the present invention comprises polyethylene oxide. In one specific embodiment of the present invention, the hydrophilic nylon copolymer comprises a nylon moiety formed from poly(pentamethylene carbonamide) (nylon 6) and polyethylene oxide formed from polyethylene oxide diamine. Such nylon-6/polyethylene oxide copolymers will suitably have a number average molecular weight within the range of from about 5,000 to 100,000, preferably from about 20,000 to about 30,000.

Polyethylene oxide diamine materials are commercially available from the Jefferson Chemical Company under the trade designation Jeffamine TM. Exemplary of other suitable hydrophilic nylon polymeric materials include a graft copolymer of nylon, such as nylon-6, and a low molecular weight poly(dimethylacrylamide), and block copolymers of nylon and a random poly(dioxaamide).

When the flow-modulating layer is formed from an intrinsically hydrophilic polymer such as the described nylon copolymers, it is preferred that the fibers of the flow-modulating layer have a heat of hydration as determined by an isoperibol calorimeter of from about 10 to about 60, preferably of from about 20 to about 40 joules per gram. Fibers having the required heat of hydration have a strong affinity for water and are best able to distribute a liquid applied thereto. The method of determining the heat of hydration is set forth below.

Alternatively, the flow-modulating layer may be formed from generally hydrophobic polymers that have been treated with a surface treatment to render them hydrophilic. Exemplary of hydrophobic polymers which may be treated to render their surface hydrophilic are polyolefins such as polypropylene and polyethylene and polyesters such as polyethylene terephthalate. A number of surface treatments are know to those skilled in the art for rendering such hydrophobic polymers generally hydrophilic. However, many of such known surface treatments are fugitive. That is, they will wash off the generally hydrophobic polymers thus exposing the hydrophobic surface of the polymer. Exemplary of nonfugitive surface treatments, which may be applied to the described hydrophobic polymers, are those surface treatments described in U.S. Pat. No. 4,578,414, issued Mar. 25, 1986, to Sawyer, et al. Hydrophobic polymeric fibers having such a generally nonfugitive surface treatment are commercially available from Dow Chemical U.S.A. under the trade designation Dow Aspun TM.

By employing hydrophilic meltblown fibers to form the fibrous flow-modulating layer, the flow-modulating layer will maintain its hydrophilic character through multiple insults of a discharged body fluid such as urine. Thus, the flow-modulating layer will desirably be able to rapidly receive three or more insults of urine without a significant change in its performance. The flow-modulating layer 28 has a dry thickness dimension 48 within the range of from about 0.02 to about 0.24 inches when measured under a restraining pressure of 0.2 pounds per square inch. Preferably, the dry thickness of the flow-modulating layer is within the range of from about 0.06 to about 0.2 inch, and more preferably within the range of from about 0.08 to about 0.16 inch to provide improved effectiveness. If the flow-modulating layer is too thick, there can be excessive bulk and excessive retention of liquids within the flow-modulating layer. If the flow-modulating layer is too thin, it may not provide a sufficient amount of flow modulation to prevent pooling and leakage and/or damage to the capillary structure of the absorbent product.

The following test methods are employed in connection with the examples which follow.

CONTACT ANGLE MEASUREMENT

The contact angle of water or synthetic urine in air of various fibrous materials are determined by one of three methods.

1) Wilhelmy Technique

Contact angles of Hydrofil TM and Pebax TM fibers are determined as set forth by Hodgson and Berg in *Wood and Fiber Science*, January, 1988, vol. 20 (1) pp. 3 to 17. A constant speed of 500 micrometers per minute is employed.

2) Optical Methods

The following method is employed to determine the contact angle of a surface treated fiber.

A two centimeter long sample of the surface treated polyethylene fiber to be tested is provided. The sample provided is attached to a fiber-holding apparatus. The fiber-holding apparatus is a 22 by 4.5 centimeter sheet of Teflon ™ having a square slot cut in one end. The fiber-holding apparatus is suspended from the end opposite the square slot such that the end containing the slot and fiber is inside a teflon container. The Teflon ™ container is filled with double distilled, double deionized water such that a meniscus is formed on the vertically oriented fiber. The Teflon ™ container and a video camera (Panasonic model WV 1550) and a variable intensity condenser light source (Olympus) sit on a movable stage. The movable stage is driven by a D. C. variable speed motor (Minarik model SL15). Damping pads are placed on the stage and under the camera to absorb any stray vibrations. The video pictures taken by the camera are recorded on high quality video tape in a video cassette recorder (Panasonic AG 6300).

The moveable stage is raised until the fiber is in contact with the water contained in the Teflon ™ container and a meniscus is formed at the interface of the water, air, and fiber. The video camera and variable intensity condenser light source are aligned to obtain a sharp image of the meniscus. A video picture of the meniscus is taken. The meniscus is then allowed to advance at a predetermined speed over the suspended fibers while meniscus shapes are recorded on the video camera. The moveable stage is then stopped and the meniscus allowed to come to a static equilibrium. After about 3-4 minutes, the image of the equilibrium contact angle is recorded by the video camera. The meniscus is now allowed to recede at a predetermined speed over the suspended fiber while lowering the moveable stage. Again, the shape of the meniscus is recorded. The moveable stage is stopped while the fiber is still in contact with the water and the meniscus is allowed to come to a static equilibrium. After about 3-4 minutes, the shape of the meniscus is recorded by the video camera. The meniscus is then quickly advanced at the same predetermined speed to obtain a dynamic contact angle on the pre-wet fiber. The experiment is repeated three times. The experiments are done at two different speeds. One is done at a relatively slow speed with an advancing meniscus speed of 0.3 milliliters per second and a receding meniscus speed of 0.4 millimeters per second, with a second set of experiments being done at a relatively fast speed with an advancing meniscus speed of 1.6 millimeters per second and a receding meniscus speed of 1.7 millimeters per second.

The pictures of the menisci are digitized and captured into an IBM-PC by PCEYE Board (Model 1150). The coordinate points describing the meniscus are obtained using image-pro software and are fed as input into a Least Square Fit Program on a VAX 8600 computer to get a suitable polynomial fit. The slope of the best polynomial fit at the contact line is used to obtain the contact angle. The values of the contact angles reported are based on extrapolation from the relatively slow and relatively fast speeds to a static (zero) speed.

3) Inferred Contact Angle

The following method is employed to determine the contact angle of carded cotton fibers and certain Hydrofil ™ fibers.

A 3 inch by 15 inch sample of the fibrous web to be tested is provided. The web has a basis weight of about 400 grams per square meter and a density of about 0.1 grams per cubic centimeter. The web is placed horizontally and one of the 3 inch ends of the sample is brought into contact with an excess of a liquid to be tested. The distance the liquid is moved horizontally along the length of the sample (wicking distance) is measured as a function of time. The sample is allowed to remain in contact with the liquid until the liquid is transported along the entire length of the sample.

The inferred contact angle of the web is based on the Washburn equation and is given by the formula:

$$x = \sqrt{\frac{R\gamma \cos\theta}{2\eta} t}$$

where
$x$ = the wicking distance;
$R$ = the mean pore size;
$\gamma$ = the surface tension of the liquid;
$\eta$ = the viscosity of the liquid;
$t$ = the time of wicking; and
$\theta$ = the contact angle of the liquid on the fiber.

The synthetic urine described below is provided. To the urine is added a surfactant commercially available from American Cyanamid Co. under the trade designation Aerosol OT ™. The surfactant is added to the urine in an amount sufficient to lower the surface tension of the synthetic urine from 56 dyne/centimeter to 25 dyne/centimeter. Because of the added surfactant the Cosine of $\theta$ equals 1. Thus, a plot of x versus the square root of t gives a linear plot with a slope equal to:

$$\sqrt{\frac{R\gamma}{2\eta}}$$

Using the synthetic urine without the addition of the Aerosol OT ™ surfactant a plot of x versus the square root of t gives a linear plot with a slope equal to:

$$\sqrt{\frac{R\gamma \cos\theta}{2\eta}}$$

By comparison of the slopes determined above, the contact angle of the synthetic urine on the fiber to be tested can be inferred.

Heat of Hydration Determination

The heat of hydration measurements are made in a Tronac Model 450 isoperibol temperature rise calorimeter. The calorimeter is modified to include a means for containing solid samples in a stainless steel ampoule sealed with two microscope slide cover slips. The calorimeter employs a 50 milliliter Dewar flask as the reaction vessel and all of the measurements are made at 25° C. The energy equivalent of the calorimeter when filled with 50 milliliters of deionized/distilled water is 7.70 joules per millivolt from electrical calibration.

The heat of hydration value is determined by weighing the fiber sample, transferring the sample into the stainless steel ampoule and attaching the ampoule to the header of the calorimeter. The Dewar flask is charged with 50 milliliters of water. The calorimeter assembly is lowered into the water bath. The calorimeter is brought up to the bath temperature by use of the calibration heater of the calorimeter, and is then allowed to come to thermal equilibrium by waiting for a period of approximately five minutes. At this point, temperature data is collected at five second intervals for the remainder of the experiment. Specifically, temperature data is collected for approximately five minutes. At this point, the cover slips sealing the stainless steel ampoules are broken to allow the samples contained in the ampoules to become wetted. Temperature data is collected for approximately another ten minutes or until the reaction is complete. Blank runs show breaking the cover slip to be negligible in terms of heat generation. The heat of hydration is reported in Joules per gram.

Fiber Diameter and Average Pore Size

The average fiber diameter and average pore size for a thin layer of material can be determined by employing a scanning electron microscope. Thin layers such as flow-modulating layers having a thickness of not more than about 0.02 inches are employed. Due to their thinness, the pore size observed at the surface of the material is believed to adequately represent the pore size of the bulk of the material. The surface measurements can be made with a scanning electron microscope employing standard techniques known to persons skilled in the art.

Figure 6:
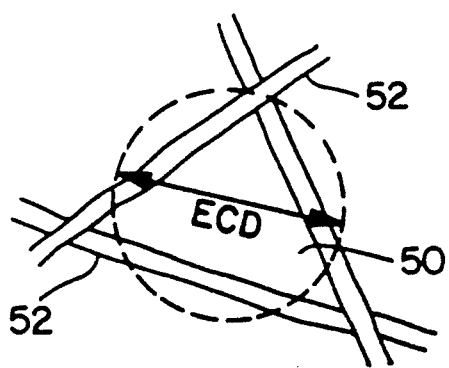
FIG. 6 illustrates the equivalent circular diameter (ECD) of a pore bounded by three fibers within a nonwoven fibrous web layer.

More particularly, a suitable technique involves separating a test sample, which measures at least 6 inches by 6 inches into 6 substantially randomly chosen pieces each measuring ½ inch by 1 inch, and then examining a major face surface of each piece. Conceptually, the major surface extends along the horizontal X-Y plane. Employing conventional techniques, the selected major surface of each piece is vapor coated with a heavy metal, such as gold, to prepare it for analysis with the electron microscope. Two fields of view are photographed from each piece to provide a total of twelve photographs. The selection of twelve random photographs provides adequate statistical stability and can be arranged to form a convenient photo montage for macro-stage automation. The choice of magnification for the photographs is not believed critical. The photographs are placed on a macro viewer of an image-analysis system, such as the Quantimet 900 Series Image-Analysis System distributed by Cambridge Instruments, Ltd. of Barhills, Cambridge CB38EL, United Kingdom. The system is set with the magnifications sufficient to examine two fields-of-view on each photograph, for a total of 24 fields. Detection (threshholding) is set for the extraction of black pores from amidst the white fiber matrix and the equipment is programmed in a conventional manner to generate a feature-specific histogram based on equivalent circular diameter (ECD). The ECD is defined as the diameter of the circle which has substantially the same area as the "pore" space 50, bounded by three or more fibers 52 (FIG. 6). At least several hundred pores, and up to several thousand pores, are then measured and analyzed with all of the individual pore ECDs accumulated into the histogram. Data values produced during the analysis can include the mean, the standard deviation, and selected percent entries in the low-end and high-end regions of the histogram.

The average pore size of the relatively thick absorbent pad is not accurately represented by a two dimensional X-Y view of the pores. By examining the absorbent pad density and absorbent fiber coarseness, however, it can be readily inferred that the average pore size in the absorbent pad is smaller than the average pore size of the other layers of the absorbent article.

The average fiber diameter is determined utilizing the scanning electron microscope generally as described above.

Fluid Intake Evaluation

Figure 7:
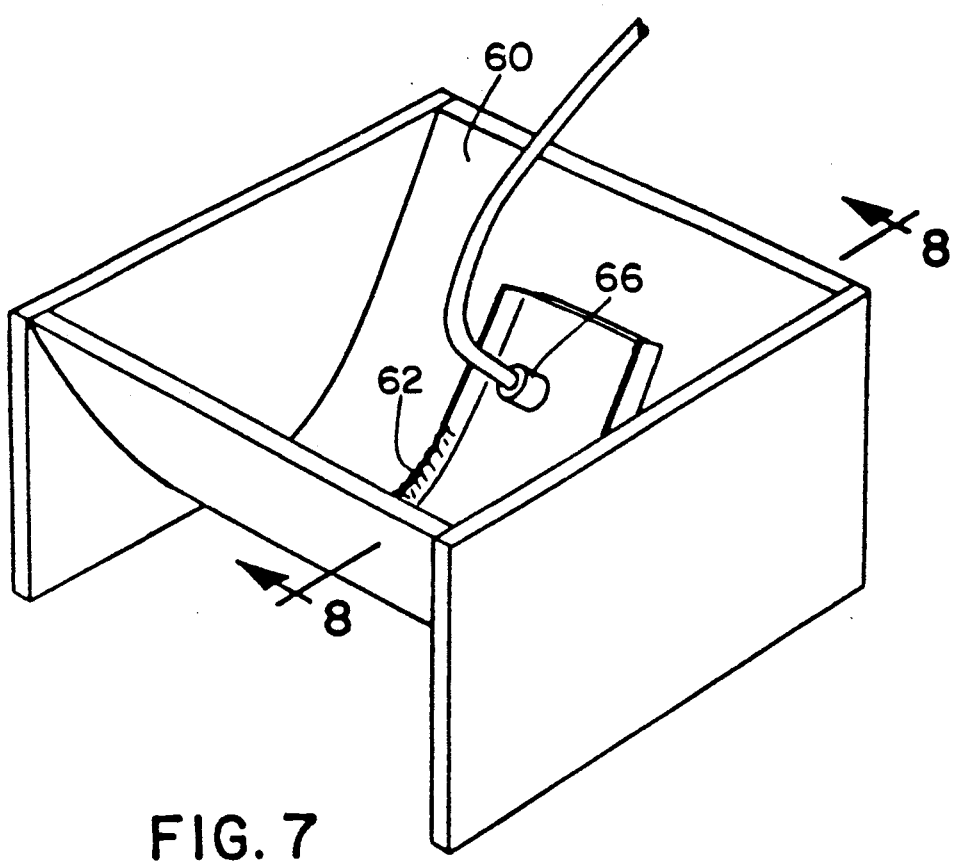
FIG. 7 illustrates the apparatus used to conduct the fluid intake evaluation.
Figure 8:
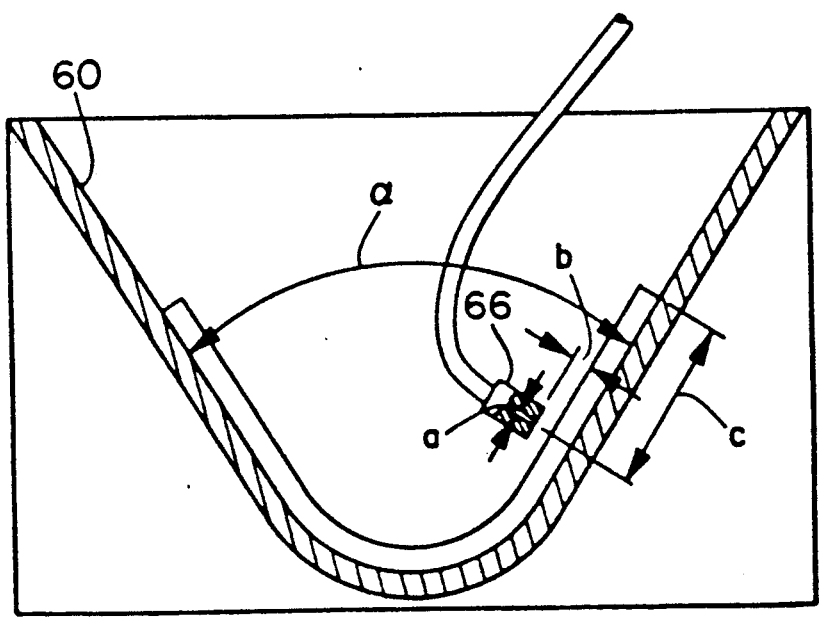
FIG. 8 is a cross-sectional view taken along Line 8—8 of FIG. 7.

The fluid intake evaluation of composites according to the present invention is determined as follows. Specifically, the fluid penetration rate is determined by providing a sample which is 9 inches long and 3 inches wide. Referring to FIG. 7, the sample is placed in a trough 60 with an included angle (alpha) of 60°. The sample is surrounded by suitable dams 62 along the sample edges to prevent fluid from running off the samples during testing. FIG. 8 is a cross-sectional view taken along line 8—8 of FIG. 7. As can be seen from reference to FIG. 8, fluid is delivered to the sample to be tested from a nozzle 66 having a 3 millimeter diameter (a) which is attached to a peristaltic pump equipped with a pulse suppressor. The nozzle is placed a distance (b) of 6 millimeters from the surface of the sample to be tested at a distance (c) of about 3.25 inches from the end of the sample to be tested such that the nozzle is generally perpendicular to the immediate adjacent surface of the sample to be tested.

The sample to be tested is subjected to three 60 milliliter insults of synthetic urine. The urine is applied through the nozzle 66 at a rate of approximately 15 milliliters per second. The time elapsed between initial fluid contact and disappearance of the fluid from the surface of the sample is measured. Absorption rate is calculated by dividing the milliliters of fluid dispensed (60) by the penetration time (time for disappearance of the fluid). The rate is reported in milliliters per second. After 15 minutes, the second insult is applied to the sample to be tested. The third insult is applied 15 minutes after application of the second insult. The fluid penetration times are reported for the first, second, and third insults. As a general rule, the faster the absorption rate (for all three insults) the better the sample would be expected to perform.

Additionally, the fluid distribution present in the flow-modulating layer of the absorbent composite is determined as follows. After receiving three insults of the synthetic urine, the insulted samples are removed from the trough. The flow-modulating layer is removed from the absorbent body and cut along its length into 9 one inch segments. The segment comprising the end of the sample closest to the nozzle is designated sample number 1 with sample number 9 being the opposite end of the sample. The amount of synthetic urine present in each of the 9 one inch segments is determined by subtracting the dry weight of the segments from the wet weight of the segment. The dry weight of the individual segments is determined by dividing the total sample dry weight determined before addition of any synthetic urine by 9 (the number of segments). The total amount of fluid retained by the flow-modulating layer is reported as the fluid residual value.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4.7H_2O$), 1.33 grams potassium sulphate ($K_2SO_4$), 1.24 grams tribasic sodium phosphate dodecahydrate ($Na_3PO_4.12H_2O$), 4.4 grams sodium chloride (NaCl), 3.16 grams potassium chloride (KCl), 8.56 grams of urea ($CO(NH_2)_2$), 0.1 rams Pluronic 10R8 surfactant (a non-ionic surfactant commercially available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

The following example is intended to give a more detailed understanding of the present invention. The following example (including comparative samples) is not intended to limit, in any manner, the scope of the claims which follow.

EXAMPLE 1

In order to determine the effectiveness of certain materials for use as flow-modulating layers, composite structures comprising an absorbent body and a flow-modulating layer are formed. One of two absorbent body structures is employed. Absorbent body A comprises an airlaid mixture of wood pulp fluff and a high absorbency polyacrylate material commercially available from Hoechst Celanese Corporation under the trade designation IM-5000P. The airlaid mixture comprises 40 weight percent of the high absorbency material and 60 weight percent of the wood pulp fluff. The retention material has a density of about 0.2 grams per cubic centimeters.

Absorbent body B comprises 75 weight percent of the high absorbency material (IM-5000P) and 25 weight percent of a meltblown hydrophilic nylon polymer commercially available from Allied-Signal, Inc. under the trade designation Hydrofil TM. Methods of forming such meltblown mixtures of high absorbency material and nylon polymeric material are known to those skilled in the art. The retention material has a density of about 0.2 grams per cubic centimeter.

The following materials are employed in forming flow-modulating layers according to the present invention. The flow-modulating layers are prepared to possess different physical properties such as basis weight, density, mean pore size, mean fiber size and the like. The exact physical properties of the various flow-modulating layers are set forth in detail in Table 1.

A first flow-modulating layer is prepared from a hydrophilic nylon polymeric material commercially available from Allied-Signal, Inc. under the trade designation Hydrofil TM SCFX. The material is a copolymer formed from nylon-6 and polyethylene oxide diamine.

A second flow-modulating layer is prepared from a meltblown polyethylene material having a hydrophilic surface treatment thereon which material is commercially available from the Dow Chemical Company under the trade designation Aspun TM.

A third flow-modulating layer is prepared from the material commercially available from Atochem Polymers Inc., Glen Rock, N.J. under the trade designation Pebax TM.

A fourth flow-modulating layer is prepared from a bonded carded web (BCW) of cotton. The web consists of 35 weight percent cotton fibers having a diameter of 14.8 microns; 50 weight percent meltblown polyethyleneterephthalate fibers having a diameter of 62 microns, and 15 weight percent of 1.5 denier Chisso ES fibers available from Chisso Corporation Japan.

A fifth flow-modulating layer was prepared comprising a mixture of 15 weight percent of Pulpex TM, a synthetic wood pulp made from polyethylene and commercially available from Hercules Inc., and 85 weight percent wood pulp fluff.

The described flow-modulating layers are prepared to assess different physical properties and are placed on either absorbent body A or B and subjected to the physical property testing described above. The exact characteristics of the sample to be tested are set forth in Table 1. The results of the physical property testing discussed above for the samples set forth in Table 1 is set forth in Table 2.

TABLE 1

| Sample No. | Absorbent Body | Flow-modulating Layer | | | | | Contact Angle | | | $\Delta H^6$ |
|---|---|---|---|---|---|---|---|---|---|---|---|
| | | Material | Basis Wt.$^1$ | Density$^2$ | Thickness$^3$ | Avg. Pore Size$^4$ | Avg. Fiber Size$^5$ | 1 | 2 | 3 | |
| 1* | A | — | — | — | — | — | — | — | — | — | — |
| 2 | A | Hydrofil TM | 200 | 0.1 | 0.08 | 200 | 51 | 0 | 0 | 0 | −31 |
| 3 | A | Hydrofil TM | 400 | 0.1 | 0.16 | 200 | 51 | 0 | 0 | 0 | −31 |
| 4 | A | Hydrofil TM | 600 | 0.1 | 0.24 | 200 | 51 | 0 | 0 | 0 | −31 |
| 5* | B | — | — | — | — | — | — | 0 | 0 | 0 | — |
| 6 | B | Hydrofil TM | 200 | 0.1 | 0.08 | 200 | 51 | 0 | 0 | 0 | −31 |
| 7 | B | Hydrofil TM | 400 | 0.1 | 0.16 | 200 | 51 | 0 | 0 | 0 | −31 |
| 8* | A | Hydrofil TM | 400 | 0.08 | 0.1 | 10 | 5 | 0 | 0 | 0 | −31 |
| 9* | A | Hydrofil TM | 400 | 0.17 | 0.09 | 67 | 30 | 0 | 0 | 0 | −31 |
| 10 | A | Hydrofil TM | 400 | 0.07 | 0.22 | 90 | 27 | 0 | 0 | 0 | −31 |
| 11 | A | Hydrofil TM | 400 | 0.1 | 0.16 | 200 | 51 | 0 | 0 | 0 | −31 |
| 12 | A | Hydrofil TM | 200 | 0.1 | 0.08 | 200 | 51 | 0 | 0 | 0 | −31 |
| 13 | A | Aspun TM | 200 | 0.1 | 0.08 | 138 | 40 | 46° | 45° | 45° | 0 |
| 14 | A | Aspun TM | 400 | 0.1 | 0.15 | 138 | 40 | 46° | 45° | 45° | 0 |
| 15 | A | Pebax TM | 400 | 0.14 | 0.11 | — | — | 31° | 31° | 31° | 72 |
| 16* | A | Cotton BCW | 200 | 0.06 | 0.13 | 67 | — | 63° | — | — | — |
| 17* | A | Pulpex TM/fluff | 150 | 0.08 | 0.07 | — | 40 | 70° | — | — | — |
| 18* | A | Pulpex TM/fluff | 300 | 0.08 | 0.15 | — | 40 | 70° | — | — | — |
| 19* | A | Pulpex TM/fluff | 450 | 0.09 | 0.2 | — | 40 | 70° | — | — | — |

*not an example of the present invention
$^1$in grams per square meter
$^2$in grams per cubic centimeter
$^3$in inches
$^4$in microns
$^5$in microns
$^6$in Joules per gram

TABLE 2

| Sample No. | Fluid Penetration Rate[1] | | | Fluid Distribution[2] | | | | | | | | | Fluid[3] Residual | Standard[4] Deviation |
|---|---|---|---|---|---|---|---|---|---|---|---|---|---|---|
| | 1 | 2 | 3 | 1 | 2 | 3 | 4 | 5 | 6 | 7 | 8 | 9 | | |
| 1* | 9.2 | 7.6 | 5.0 | — | — | — | — | — | — | — | — | — | — | — |
| 2 | 11.9 | 11.5 | 9.5 | 0.2 | 0.3 | 0.35 | 0.45 | 0.55 | 0.45 | 0.35 | 0.3 | 0.2 | 3.10 | 0.11 |
| 3 | 12.9 | 12.6 | 12 | 0.4 | 0.6 | 0.7 | 0.75 | 0.17 | 0.8 | 0.76 | 0.5 | 0.25 | 5.53 | 0.18 |
| 4 | 14.5 | 12.6 | 12.1 | 0.6 | 0.75 | 1.0 | 1.2 | 1.2 | 1.2 | 0.75 | 0.5 | 0.1 | 7.30 | 0.36 |
| 5* | 7.5 | 4.7 | 3 | — | — | — | — | — | — | — | — | — | — | — |
| 6 | 11.3 | 9.4 | 6.3 | — | — | — | — | — | — | — | — | — | — | — |
| 7 | 11.9 | 11.6 | 10.2 | — | — | — | — | — | — | — | — | — | — | 0.4 |
| 8* | 8.9 | 6.9 | 5.1 | — | — | — | — | — | — | — | — | — | — | |
| 9* | 13.1 | 10.9 | 9.2 | 0.4 | 0.8 | 0.9 | 1.1 | 1.0 | 0.8 | 0.8 | 0.7 | 0.5 | 7.0 | 0.17 |
| 10 | 11.9 | 11.7 | 11.6 | 0.43 | 0.83 | 1.27 | 1.62 | 1.72 | 1.27 | 1.08 | 0.56 | 0.4 | 9.18 | 0.47 |
| 11 | 12.9 | 12.6 | 12.0 | 0.4 | 0.6 | 0.7 | 0.75 | 0.77 | 0.8 | 0.76 | 0.5 | 0.25 | 5.53 | 0.18 |
| 12 | 12.3 | 12.0 | 11.4 | 0.15 | 0.19 | 0.3 | 0.38 | 0.45 | 0.38 | 0.32 | 0.2 | 0.12 | 2.49 | 0.11 |
| 13 | 11.7 | 11.8 | 10.8 | 0.1 | 0.1 | 0.1 | 0.14 | 0.1 | 0.13 | 0.1 | 0 | 0 | 0.67 | 0.05 |
| 14 | 12.7 | 12.1 | 12.0 | 0.05 | 0.06 | 0.15 | 0.24 | 0.2 | 0.21 | 0.07 | 0 | 0 | 0.98 | 0.09 |
| 15 | 11.4 | 10.7 | 10.5 | 0.05 | 0.05 | 0.41 | 0.94 | 1.48 | 1.44 | 0.86 | 0.1 | 0.1 | 5.43 | 0.56 |
| 16* | 12.2 | 12.0 | 11.2 | 0 | 0 | 0.4 | 1.10 | 1.20 | 1.15 | 0.9 | 0.05 | 0 | 4.8 | 0.51 |
| 17* | 12.0 | 11.8 | 8.2 | 0 | 0.3 | 5.6 | 7.0 | 7.0 | 5.0 | 2.6 | 0 | 0 | 27.5 | 2.93 |
| 18* | 12.0 | 11.0 | 9.0 | 0 | 0 | 2.6 | 5.0 | 6.3 | 5.5 | 3.3 | 0.3 | 0 | 23.0 | 2.45 |
| 19* | 13 | 11.8 | 10.8 | 0 | 0.3 | 5.5 | 6.6 | 5.5 | 4.4 | 1.6 | 0 | 0 | 23.9 | 2.64 |

*not an example of the present invention
[1] in milliliters per second
[2] in grams
[3] total fluid remaining in flow-modulating layer in grams
[4] standard deviation value of the fluid distribution data As can be seen from reference to Tables 1 and 2, composite structures according to the present invention perform generally better than the comparative samples. As discussed above, it is desirable that the flow-modulating layer not retain an excessive amount of liquid. This is reflected in the fluid residual data of Table 2. If the flow-modulating layer retains an excessive amount of fluid, it is more difficult for the layer to absorb subsequent insults of liquid. Moreover, it is desirable that the layer have a relatively small standard deviation thereby generally indicating good distribution of the fluid throughout the flow-modulating layer. The standard deviation is suitably less than about 1.0.

What is claimed is:

1. An absorbent article, said article comprising:
   an absorbent body capable of absorbing a liquid, said absorbent body having an average pore size therein;
   a liquid-permeable body-side liner superposed in facing relation with said absorbent body; and
   a fibrous flow-modulating layer for modulating the flow of said liquid, said flow-modulating layer being in liquid communication with said absorbent body, being located between said absorbent body and said body-side liner and consisting essentially of hydrophilic meltblown fibers having an average diameter of from about 20 to about 60 microns, said flow-modulating layer having an average pore size of from about 90 to about 300 microns and a basis weight of from about 50 to about 600 grams per square meter, wherein the average pore size of said absorbent body is less than the average pore size of said flow-modulating layer.

2. The absorbent article according to claim 1 wherein said hydrophilic meltblown fiber is formed from a polymeric material selected from the group consisting of hydrophilic nylon copolymers, polyolefins having a nonfugitive hydrophilic surface treatment thereon and polyesters having a nonfugitive hydrophilic surface treatment thereon.

3. The absorbent article according to claim 2 wherein said nylon copolymer is a block copolymer comprising a nylon moiety and a hydrophilizing polymeric moiety.

4. The absorbent article according to claim 3 wherein said nylon copolymer is a block copolymer comprising poly(pentamethylene carbonamide) and polyethylene oxide diamine.

5. The absorbent article according to claim 3 wherein said hydrophilizing polymeric moiety comprises polyethylene oxide.

6. The absorbent article according to claim 1 wherein said absorbent body comprises wood pulp fluff and a high-absorbency material.

7. The absorbent article according to claim 6 wherein said absorbent body has a density within the range of from about 0.05 to about 0.3.

8. The absorbent article according to claim 1 wherein said hydrophilic meltblown fiber has a contact angle of water in air of less than about 10 degrees.

9. The absorbent article according to claim 1 wherein said flow-modulating layer has a basis weight of from about 100 to about 400 grams per square meter.

10. The absorbent article according to claim 9 wherein said hydrophilic meltblown fibers have an average diameter within the range of from about 40 to about 60 microns.

11. The absorbent article according to claim 10 wherein said flow-modulating layer has an average thickness within the range of from about 0.02 to about 0.24.

12. The absorbent article according to claim 11 wherein said hydrophilic meltblown fiber is formed from a block copolymer comprising poly(pentamethylene carbonamide) and polyethylene oxide diamine.

13. The absorbent article according to claim 1 wherein said flow-modulating layer has a fluid distribution standard deviation value of less than about 1.0.

14. The absorbent article according to claim 1 wherein said flow-modulating layer has a fluid residual value of less than about 10.

15. An absorbent article, said article comprising:
   an absorbent body capable of absorbing a liquid, said absorbent body having an average pore size therein; and
   a fibrous flow-modulating layer for modulating the flow of said liquid, said flow-modulating layer being in liquid communication with said absorbent body and consisting essentially of hydrophilic meltblown fibers having an average diameter of from about 20 to about 60 microns, said flow-modulating layer having an average pore size of from about 90 to about 300 microns, and a basis weight of from about 50 to about 600 grams per square meter, an average thickness of from about 0.02 to about 0.24 inch wherein the average pore size of said absorbent body is less than the average pore size of said flow-modulating layer.

16. The absorbent article according to claim 15 wherein said hydrophilic meltblown fiber is formed from a polymeric material selected from the group consisting of hydrophilic nylon copolymers, polyolefins having a nonfugitive hydrophilic surface treatment thereon, and polyesters having a nonfugitive hydrophilic surface treatment thereon.

17. The absorbent article according to claim 16 wherein said hydrophilic nylon copolymer is a block copolymer comprising a nylon moiety and a hydrophilizing polymeric moiety.

18. The absorbent article according to claim 17 wherein said nylon copolymer is a block copolymer comprising poly(pentamethylene carbonamide) and polyethylene oxide diamine.

19. The absorbent article according to claim 17 wherein said hydrophilizing polymeric moiety comprises a polyethylene oxide.

20. The absorbent article according to claim 15 wherein said absorbent body comprises wood pulp fluff and a high-absorbency material.

21. The absorbent article according to claim 20 wherein said absorbent body has a density within the range of from about 0.05 to about 0.3.

22. The absorbent article according to claim 15 wherein said hydrophilic fiber has a contact angle of water in air of less than about 10 degrees.

23. The absorbent article according to claim 15 wherein said flow-modulating layer has a basis weight of from about 100 to about 400 grams per square meter.

24. The absorbent article according to claim 23 wherein said hydrophilic meltblown fibers have an average diameter within the range of from about 40 to about 60 microns.

25. The absorbent article according to claim 24 wherein said flow-modulating layer has an average thickness within the range of from about 0.02 to about 0.24.

26. The absorbent article according to claim 25 wherein said hydrophilic meltblown fiber is formed from a block copolymer formed from poly(pentamethylene carbonamide) and polyethylene oxide diamine.

27. The absorbent article according to claim 15 wherein said flow-modulating layer has a fluid distribution standard deviation value of less than about 1.0.

28. The absorbent article according to claim 15 wherein said flow-modulating layer has a fluid residual value of less than about 10.

* * * * *